United States Patent [19]
Cihonski

[11] 4,429,175
[45] Jan. 31, 1984

[54] PROCESS FOR THE PRODUCTION OF ETHYLBENZENE

[75] Inventor: John L. Cihonski, Odessa, Tex.

[73] Assignee: El Paso Products Company, Odessa, Tex.

[21] Appl. No.: 437,029

[22] Filed: Oct. 27, 1982

[51] Int. Cl.³ .................................................. C07C 5/41
[52] U.S. Cl. ..................................... 585/433; 585/434
[58] Field of Search ................................ 585/433, 434

[56] References Cited

U.S. PATENT DOCUMENTS

| 3,376,215 | 4/1968 | Bertolacini et al. | 585/434 |
|---|---|---|---|
| 3,502,736 | 3/1970 | Sato et al. | 585/434 |
| 3,903,185 | 9/1975 | Vogel et al. | 585/434 |
| 4,300,010 | 11/1981 | Cihonski | 585/434 |
| 4,359,594 | 11/1982 | Patterson et al. | 585/434 |

Primary Examiner—Delbert E. Gantz
Assistant Examiner—Cynthia A. Prezlock
Attorney, Agent, or Firm—Depaoli & O'Brien

[57] ABSTRACT

This invention provides a process for selective conversion of vinylcyclohexene to ethylbenzene and hydrogen in the presence of a palladium on non-acidic zeolite catalyst.

In the catalyst preparation, the catalyst is calcined first in air and then in a hydrocarbon type environment. Without the two step calcination procedure, the catalyst has a lower level of activity and selectivity.

The process proceeds as an oxygen-assisted dehydrogenation reaction which yields recoverable hydrogen byproduct, rather than as an oxydehydrogenation reaction which yields water byproduct.

7 Claims, No Drawings

PROCESS FOR THE PRODUCTION OF ETHYLBENZENE

BACKGROUND OF THE INVENTION

The importance of styrene as a large volume organic commodity has stimulated increasing efforts to develop new and improved methods for efficient synthesis of the compound.

In many of the processes contemplated for styrene synthesis, vinylcyclohexene or ethylbenzene function as starting materials or as key intermediates.

U.S. Pat. No. 2,976,331 describes a method for simultaneously effecting the catalytic dehydrogenation of a naphthenic hydrocarbon to an aromatic and the catalytic hydrogenation of an olefin to paraffins which involves contacting a naphthene/olefin mixture at 350°–850° F. with a crystalline metallo-alumino-silicate catalyst having uniform pores of 10–13 angstroms.

U.S. Pat. No. 3,502,736 describes a method for the oxidative dehydrogenation of a nonaromatic cyclic hydrocarbon having at least one unsaturated bond in a side chain, which method consists of contacting the said cyclic hydrocarbon in the presence of oxygen with a catalyst consisting of palladium oxyhydrate. In Example 1, the conversion rate of vinylcyclohexene is 86.8 percent, and the selectivity to styrene is 91.3 percent.

U.S. Pat. No. 3,903,185 describes a dehydrogenation process which is reported to be capable of converting vinylcyclohexene to ethylbenzene with a 96.6 percent selectivity. The process parameters include a 350°–450° C. temperature, a 2.5–30 atmospheres pressure, 0.2–20 m$^3$ of hydrogen/kg of vinylcyclohexene, and a catalyst containing metal elements selected from subgroups VI–VIII of the periodic table.

U.S. Pat. No. 4,163,761 describes a liquid phase process which involves converting vinylcyclohexene to styrene at a temperature of 170°–360° C. in the presence of a nitro compound and a copper chromite catalyst. The Example 1 data indicate a 19.2 percent selectivity of vinylcyclohexene to styrene, and a 7.5 percent selectivity to ethylbenzene.

U.S. Pat. No. 4,165,441 describes a vapor phase process for converting vinylcyclohexene to styrene which involves contacting vinylcyclohexene with oxygen in the presence of a tin-antimony oxide catalyst. A typical result in Table 1 indicates 82.4 percent vinylcyclohexene conversion, and a product selectivity of 58.9 percent styrene and 6 percent ethylbenzene, respectively.

Other United States patents of general interest with respect to dehydrogenation technology include U.S. Pat. Nos. 2,392,960; 2,404,104; 2,438,041; 2,560,329; 3,236,903; 3,409,960; 3,437,703; 3,511,885; and references cited therein.

The prior art vinylcyclohexene dehydrogenation processes characteristically produce mixtures of styrene and ethylbenzene, and usually only partial conversions are achieved. In many cases good conversion rates are counterbalanced by short-lived catalyst activity. Further, high temperatures and pressures cause cracking and isomerization side reactions. Objectional amounts of benzene, toluene and xylene are formed, and these are difficult to separate from ethylbenzene. Some processes require the use of hydrogen, which adversely affects the economics of a process.

U.S. Pat. No. 4,300,010 describes a process for conversion of vinylcyclohexenes to ethylbenzene which overcomes many of the disadvantages of prior art vinylcyclohexene dehydrogenation processes. The U.S. Pat. No. 4,300,010 process involves the use of molecular oxygen and a catalyst consisting of palladium supported on a non-acidic zeolite carrier substrate, wherein the catalyst has been subjected to a specific pretreatment calcination procedure.

The U.S. Pat. No. 4,300,010 process is essentially a oxydehydrogenation reaction, characterized by the production of water as a byproduct, and consequentially a low production of hydrogen byproduct. The present invention process is related to the U.S. Pat. No. 4,300,010 process, and represents a further embodiment adapted to provide various additional process advantages.

Accordingly, it is an object of this invention to provide a process which is adapted to convert vinylcyclohexene with a high selectivity to ethylbenzene under relatively mild conditions.

It is a further object of this invention to provide a process for efficient conversion of vinylcyclohexene to ethylbenzene, with the concomitant production of recoverable hydrogen byproduct, and with the substantial absence of water byproduct formation.

Other objects and advantages of the present invention shall become apparent from the accompanying description and examples.

DESCRIPTION OF THE INVENTION

One or more objects of the present invention are accomplished by the provision of a process for the conversion of vinylcyclohexene to ethylbenzene and hydrogen which comprises contacting the vinylcyclohexene with between about 1–15 mole percent of molecular oxygen per mole of vinylcyclohexene, at a temperature in the range between about 190°–260° C. in the presence of a catalyst comprising palladium supported on a non-acidic zeolite carrier substrate; wherein the said catalyst has been pretreated by calcination in a molecular oxygen-containing atmosphere and then by calcination in a hydrogen or $C_1$–$C_{10}$ nonaromatic hydrocarbon-containing atmosphere prior to vinycyclohexene conversion.

The term "vinylcyclohexene" refers to a feedstock which contains a substantial proportion of 4-vinylcyclohexene-1 (e.g., butadiene dimer as illustrated in U.S. Pat. No. 2,544,808). The feed material may include components such as propane or benzene which are non-reactive under the process conditions; and may include components which are reactive under the process conditions such as n-butane, isobutane, n-butenes, isobutylene, butadiene, n-octenes, 2-vinylcyclohexene, 3-vinylcyclohexene, ethylcyclohexane, and the like.

In reference to the catalyst composition employed in the process, the term "non-acidic" zeolite is meant to include alkali metal and alkaline earth metal forms of zeolites having a pore size less than about 5 angstrom units (5 Å) as a preferred type of carrier substrate component.

Assuming in zeolites one equivalent per aluminum atom, the equivalent ratio of alkali or alkaline earth metal to aluminum is nominally 1±0.05. This corresponds to 95 percent or more protonic sites (H+) which are substituted by atoms selected from alkali and alkaline earth metal cations such as Na+, K+, Ca++, Mg++, and the like.

Illustrative of non-acidic zeolite substrates suitable for the practice of the present invention vinylcyclohexene conversion process are alkali metal and alkaline earth metal forms of various natural and synthetic crystalline aluminosilicates known in the prior art, such as zeolite A, analcime, chabazite, gmelinite, harmotome, levynite, mordenite, and the like.

The preparation of zeolite A is described in U.S. Pat. No. 3,882,243. The structure, chemistry and use of natural and synthetic zeolites is presented in "Zeolite Molecular Sieves", D. W. Breck (John Wiley & Sons, New York, 1974).

Catalyst Preparation

In the manner described in U.S. Pat. No. 4,300,010, the present invention catalyst can be prepared conveniently by slurrying an appropriate quantity of commercial non-acidic zeolite in an aqueous solution of a water-soluble or partially water-soluble compound of palladium. The pH of the slurry is adjusted into the alkaline range, and the slurry is stirred with mild heating for a period up to about one hour. The catalyst precursor solids are drained, and oven dried at a temperature above about 100° C.

The dried catalyst precursor solids are then calcined in air (i.e., molecular oxygen) at a temperature between about 400°–600° C. for a period between about 0.5–10 hours. The weight percent of palladium in the catalyst composition can vary in the range between about 0.1–5, based on the composition weight.

It is an essential feature of the present invention catalyst preparation that the calcination of the catalyst in the presence of molecular oxygen must be followed by calcination of the catalyst in a hydrogen or $C_1$–$C_{10}$ nonaromatic hydrocarbon-containing atmosphere. Illustrative of suitable $C_1$–$C_{10}$ nonaromatic hydrocarbons are alkanes such as ethane, propane, butane, isobutane, pentane, hexane, cyclohexane, octane, decane, and the like. The said hydrocarbons can contain heteroatoms such as oxygen, nitrogen and halogen which are non-interfering under the calcination conditions. Although non preferred, an aromatic-substituted alkane can also be employed. e.g., ethylbenzene.

The said essential calcination of the catalyst in a hydrogen or nonaromatic hydrocarbon atmosphere is conducted at a temperature between about 450°–600° C. for a period between about 0.5–10 hours.

The resultant calcined catalyst matrix can be formed into the shape of granules, pellets, extrudate, powders, tablets, fibers, or other such convenient physical structure.

If the sequence of calcination steps described above is not performed, then the catalyst that is obtained is not in accordance with the practice of the present invention. Such a nonconforming catalyst tends to exhibit less reactivity and selectivity, and further, the said catalyst tends to have a shorter period of sustained activity in a continuous processing system for vinylcyclohexene conversion to ethylbenzene.

Vinylcyclohexane Conversion

Suitable reactors for the vapor phase conversion of vinylcyclohexene include either fixed bed or fluid bed reactors which contain the palladium on non-acidic zeolite carrier catalyst component. The gas fed to the reactors comprises vinylcyclohexane and molecular oxygen to which nitrogen, carbon dioxide, steam or the like may optionally be added as an inert diluent. Any vinylcyclohexene feed which remains unreacted can be recycled in the process if desired.

The dehydrogenation reaction is conducted at a temperature in the range between about 190°–260° C., and preferably at a temperature of about 200°–240° C. The pressure can vary in the range between about 1–200 psi.

In a continuous process, the residence time (i.e., catalyst contact time) of the feed stream normally will be in the range between about 0.5 and 10 seconds, and preferably in the range between about 1 and 5 seconds. Residence time refers to the contact time adjusted to 25° C. and atmospheric pressure. The contact time is calculated by dividing the volume of the catalyst bed (including voids) by the volume per unit time flow rate of the feed stream at NTP.

In terms of liquid hourly space velocity (LHSV), the flow rate of the vinylcyclohexane nominally will be in the range between about 5–20 v/v/hr.

In the present invention process, the optimal conversion and selectivity of vinylcyclohexene to ethylbenzene and hydrogen is achieved if the quantity of molecular oxygen employed is less than about 20 mole percent per mole of vinylcyclohexene feed. Preferably, the quantity of molecular oxygen employed is in the range between about 1–15 mole percent per mole of vinylcyclohexene feed.

It is not necessary to use pure oxygen as the source of oxygen. Air is a suitable source of oxygen and is desirable for reasons of economy. Alternatively, the oxidizing agent can be ozone (under conditions which prevent direct interaction of ozone and olefin) or a compound which can generate oxygen under reaction conditions (e.g., peroxides and hydroperoxides).

An essential aspect of the present invention is the less than stoichiometric quantity of molecular oxygen which is used in comparison with the vinylcyclohexene feed being dehydrogenated. As demonstrated in U.S. Pat. No. 4,300,010, when a 1:1 molar ratio of vinylcyclohexene/molecular oxygen is reacted under the processing conditions, an oxydehydrogenation reaction occurs and there is a resultant yield of water byproduct, and only a low yield of hydrogen byproduct.

The present invention process differs in that the mechanism of reaction is an oxygen-assisted dehydrogenation reaction. The result is a yield of between about 1–3 moles of hydrogen byproduct per mole of vinylcyclohexene which is fed into the dehydrogenation system, and the substantial absence of water byproduct formation.

Several advantages derive from the oxygen-assisted dehydrogenation process of the present invention:

(1) there is a lower energy input because a lower initial temperature (e.g., about 200° C.) can be employed for the present invention dehydrogenation reaction as compared to the higher initial temperature required for an oxydehydrogenation reaction;

(2) only a small volume of diluent gas (e.g., air) is necessary for purposes of the present invention process, which thereby facilitates the low temperature dehydrogenation reaction and the subsequent separation of the product mixture components;

(3) the hydrogen byproduct has recoverable value, as opposed to water byproduct which can also represent a disposal problem; and (4) at the lower dehydrogenation reaction temperature permitted by the present invention process there is a greater selectivity to the desired products than there is at a correspondingly higher dehydrogenation temperature at which level side reactions such as cracking and isomerization are more prevalent.

The following examples are further illustrative of the present invention. The reactants and other specific ingredients are presented as being typical, and various modifications can be derived in view of the foregoing disclosure within the scope of the invention.

rapidly. Also, as the molecular oxygen content of the feedstream is increased, the conversion rate decreases to some degree, and the yield of water byproduct increases and the yield of hydrogen byproduct decreases (i.e., approaches zero formation).

TABLE I

| Run | Temp. (°C.) | LHSV[1] | VCH/ $O_2$[2] | VCH Conv. (wt %) | VCH Ty[3] | EB[4] | Sty[5] | Unk[6] |
|---|---|---|---|---|---|---|---|---|
| | | | | | Selectivities (wt %) | | | |
| 1 | 195 | 1 | 1 | 98.3 | 2 | 98 | tr | tr |
| 2 | 210 | 1 | 1 | 99.6 | 1 | 99 | tr | tr |
| 3 | 225 | 2 | 1 | 91.9 | 2 | 95 | 3 | — |
| 4 | 230 | 2 | 1 | 81.5 | 1 | 87 | 12 | tr |
| 5 | 210 | 3 | 1 | 78.7 | 2 | 87 | 11 | tr |
| 6 | 220 | 4 | 1 | 51.1 | 5 | 58 | 37 | tr |
| 7 | 200 | 1 | 1 | 99.7 | 2 | 97 | 1 | tr |
| 8 | 210 | 2 | 1 | 86.5 | 1 | 83 | 16 | tr |
| 9 | 205 | 3 | 1 | 91.3 | 2 | 93 | 5 | tr |
| 10 | 211 | 4 | 1 | 66.8 | 2 | 73 | 25 | tr |

[1]LHSV = Liquid Hour Space Velocity of VCH
[2]Mole Ratio
[3]VCH Ty = Components Related to VCH Such as Ethylcyclohexene, but not VCH
[4]Ethylbenzene
[5]Styrene
[6]Unk = Unknowns, species heavier than styrene. In most cases this consists mainly of acetophenone.

EXAMPLE I

This Example illustrates the preparation of a palladium catalyst, and the selective conversion of vinylcyclohexene (VCH) to ethylbenzene in accordance with the disclosure of U.S. Pat. No. 4,300,010.

A slurry admixture is prepared employing 10 percent palladium chloride solution ($PdCl_2$, 5 grams), Linde 3A zeolite (88 grams) and water (100 grams). The pH of the slurry admixture is adjusted to 8-10 with ammonium hydroxide, and the admixture is heated for 15-20 minutes with stirring. The catalyst percursor solids are recovered, washed with water, dried for 18 hours at 110° C., and calcined in air at 500° C. for 4 hours. The catalyst is then calcined in a propane atmosphere at 550° C. for one hour.

The recovered catalyst is crushed and sieved to yield 20-30 mesh catalyst particles. About 15 cm³ of the catalyst composition is charged to a 7 mm I.D. glass tube reactor.

Vinylcyclohexene is contacted with the catalyst in the reactor under the conditions and with the results indicated in Table I.

As illustrated in Table I, the vinylcyclohexene conversion rate decreases slightly as the LHSV is increased, and the selectivity to ethylbenzene decreases in favor of styrene.

Other related process runs indicate that if the reaction temperature is lowered much below 200° C. (e.g., 143° C.) the vinylcyclohexene conversion rate drops off

EXAMPLE II

This Example illustrates an oxygen-assisted dehydrogenation of vinylcyclohexene reaction conducted in accordance with the present invention.

A catalyst is prepared in the manner described in Example I. The final form of the catalyst consists essentially of 0.01 weight percent palladium on Linde 3A zeolite.

A series of vinylcyclohexene dehydrogenation runs are performed, and the results are as summarized in Table II.

The data indicate that an approximate minimum of 1.0 mole percent molecular oxygen, per mole of vinylcyclohexene is required for catalyst activity. Runs 1a and 1b in Table II illustrate the difference in results as between the presence or absence of molecular oxygen in the dehydrogenation zone. When nitrogen flow is substituted for air flow, a rapid drop in reaction temperature occurs.

Runs 2-6 illustrate conversion and selectivity results under oxygen deficient conditions and varied liquid hour space velocity (LHSV).

Each vinylcyclohexene stream in the Table II runs is fed at 200° C., and the variation of reaction temperature appears to be a function of feed rate and the heat flow characteristics of the reactor. The overall dehydrogenation reaction is exothermic. The generation of hydrogen byproducts parallels the liquid flow rates.

TABLE II

| Run | Temp. (°C.)[1] | VCH LHSV[2] | VCH/ $O_2$[3] | VCH Conv.[4] | EB | Sty | VCH Ty[5] | Co, $CO_2$ | $H_2$[6] |
|---|---|---|---|---|---|---|---|---|---|
| 1a | 263-267 | 5.8 | 0.45/0.11 | 97 | 96 | 0.1 | 4 | 0.1 | 0.53 |
| b | 260-138 | 5.9 | 0.46/0.00 $N_2$ Run | 2 | 56 | — | 37 | — | 0 |
| 2 | 269-273 | 8.2 | 0.63/0.01 | 96 | 89 | 0.1 | 11 | 0.1 | 1.2 |
| 3 | 254-301 | 10.4 | 0.80/0.01 | 76 | 85 | 0.1 | 15 | 0.1 | 0.75 |
| 4 | 305 | 12.0 | 0.92/0.01 | 72 | 87 | 0.1 | 13 | 0.1 | 1.25 |
| 5 | 303 | 13.7 | 1.05/0.01 | 70 | 88 | 0.1 | 12 | 0.1 | 2.18 |

TABLE II-continued

| Run | Temp. (°C.)[1] | VCH LHSV[2] | VCH/ $O_2$[3] | VCH Conv.[4] | EB | Sty | VCH Ty[5] | Co, $CO_2$ | $H_2$[6] |
|---|---|---|---|---|---|---|---|---|---|
| 6 | 298 | 16.2 | 1.24/0.01 | 65 | 86 | 0.1 | 14 | 0.1 | 4.2 |

[1] Temperature at the center of a 10 ml catalyst bed.
[2] LHSV = Liquid Hour Space Velocity.
[3] Units are mole VCH/Hr and Mole $O_2$/Hr.
[4] Conversion is based on the weight of VCH fed.
[5] The major component is ethylcyclohexene. VCH = VCH Type compounds, those which can go on to form EB.
[6] $H_2$ generation is in moles $H_2$/hr.

The catalyst is reactivated easily by recalcining, i.e., four hours in air at 500° C., and two hours in propane at 550° C. The regenerated catalyst has substantially the same reactivity and selectivity as the original catalyst.

When 0.06 and 0.3 weight percent palladium on Linde 3A zeolite catalysts are life-tested over a two week period of continuous vinyl cyclohexene dehydrogenation, the catalysts are only partially deactivated. The conversion rate decreases about 10 percent over the two week period, while the selectivity performance remains approximately the same.

The two week test period results also indicate that at a palladium content above about 0.005 weight percent the catalyst is effective for greater than 90 percent vinylcyclohexene conversion and selectivity to ethylbenzene at a LHSV of about 5, as long as about 1–15 mole percent of molecular oxygen per mole of vinylcyclohexene is employed. At less than 1.0 mole percent molecular oxygen per mole of vinylcyclohexene, the activity of the catalyst decreases sharply. As the molecular oxygen increases above about 15 mole percent per mole of vinylcyclohexene, high conversion and selectivity to ethylbenzene is obtained but the hydrogen byproduct formation decreases and the water byproduct formation increases.

What is claimed is:

1. A process for the conversion of vinylcyclohexene to ethylbenzene and hydrogen which comprises contacting the vinylcyclohexene with between about 1–15 mole percent of molecular oxygen per mole of vinylcyclohexene, at a temperature in the range between about 190°–260° C. in the presence of a catalyst comprising palladium supported on a non-acidic zeolite carrier substrate; wherein the said catalyst has been pretreated by calcination in a molecular oxygen-containing atmosphere and then by calcination in a hydrogen or $C_1$–$C_{10}$ nonaromatic hydrocarbon-containing atmosphere prior to vinylcyclohexene conversion, and wherein the said catalyst subsequently is reactivated by application of the said calcination procedure to provide a regenerated catalyst which exhibits substantially the same reactivity and selectivity as the original catalyst in the process.

2. A process in accordance with claim 1 wherein the conversion of vinylcyclohexene is at least 70 percent, and the selectivity to ethylbenzene is at least 85 percent.

3. A process in accordance with claim 1 wherein between about 1–3 moles of hydrogen are produced per mole of vinylcyclohexene feed.

4. A process in accordance with claim 1 wherein the liquid hourly space velocity (LHSV) of the vinylcyclohexene is in the range between about 5–20 v/v/hr.

5. A process in accordance with claim 1 wherein the carrier substrate is a non-acidic zeolite having a pore size which is less than about 5 angstrom units.

6. A process in accordance with claim 1 wherein the carrier substrate is zeolite A.

7. A process in accordance with claim 1 wherein the catalyst is pretreated by calcination in air at a temperature between about 400°–600° C., and then by calcination in a $C_1$–$C_{10}$ nonaromatic hydrocarbon atmosphere at a temperature between about 450°–600° C.

* * * * *